United States Patent [19]
Tran

[11] Patent Number: 5,274,728
[45] Date of Patent: Dec. 28, 1993

[54] HEAVY METAL-OXIDE GLASS OPTICAL FIBERS FOR USE IN LASER MEDICAL SURGERY

[75] Inventor: Danh C. Tran, Bethesda, Md.

[73] Assignee: Infrared Fiber Systems, Inc., Silver Spring, Md.

[21] Appl. No.: 909,380

[22] Filed: Jul. 6, 1992

[51] Int. Cl.$^5$ .............................................. G02B 6/00
[52] U.S. Cl. ................................... 385/142; 385/141; 501/37; 501/41
[58] Field of Search .................. 385/141, 142, 123; 501/37, 47

[56] References Cited

U.S. PATENT DOCUMENTS

| | | | |
|---|---|---|---|
| 4,846,172 | 7/1989 | Berlin | 128/303.1 |
| 4,988,163 | 1/1991 | Cohen et al. | 350/96.29 |
| 5,164,945 | 11/1992 | Long et al. | 385/39 |

FOREIGN PATENT DOCUMENTS

| | | | |
|---|---|---|---|
| 0072404 | 6/1981 | Japan | 501/37 |
| 0213640 | 12/1984 | Japan | 501/42 |

OTHER PUBLICATIONS

Scientific American, "Infrared Optical Fibers" pp. 110-116, Nov. 1988.

S. May. "Expanding Laser Applications Foster Technological Evolution", Photonics Spectra, Nov. 1991.

L. Esterowitz, et al. "Angioplasty With a Laser and Fiber Optics ... ", vol. 622 SPIE, Jan. 1986.

H. Takahashi, et al. "Decreased Losses in Germanium-Oxide Glass Optical Fiber ... ". Japanese Journal of Applied Physics. vol. 22, No. 3, Mar. 1983 pp. L139-L140.

M. D. Rigterink. "Material Systems, Fabrication and Characteristics ... Waveguides". Ceramic Bulletin, vol. 55, No. 9 (1976), pp. 775-780.

*Primary Examiner*—Frank Gonzalez
*Assistant Examiner*—Stephen W. Barns
*Attorney, Agent, or Firm*—Sheridan Neimark Browdy and Neimark

[57] ABSTRACT

An improved optical fiber for transmitting mid-infrared wavelength laser light in surgical instruments, includes, a heavy-metal oxide component, preferably $GeO_2$ doped with heavier cations and anions, is capable of delivering of at least three watts of laser power continuously for more than ten minutes, without failure. This glass fiber has an $\alpha(dB/m)$ at $2.94\mu m$ of 10, preferably less, and can transmit at least 27% of the IR through a thickness of one foot.

9 Claims, 10 Drawing Sheets

HEAVY METAL-OXIDE GLASS OPTICAL FIBERS FOR USE IN LASER MEDICAL SURGERY

FIELD OF INVENTION

The present invention relates to improved IR transmitting fibers and, more particularly, to the use of oxide and heavy-metal containing glass fibers for coupling with a mid-infrared laser for medical laser surgical applications.

BACKGROUND OF THE INVENTION

Laser microsurgery and coronary angioplasty require precise removal of tissue without thermally damaging the surrounding tissues. Such medical/surgical lasers require using a wavelength in the mid-infrared wavelength region, i.e. between about 1.0 and 3.0 microns, which is the wavelength range most strongly absorbed by animal tissue. The 2.94 micron wavelength of the Er:Yag laser is the most well-absorbed by animal tissue and thus the Er:Yag laser is preferred for many surgical procedures.

The tissue absorption coefficient ($\alpha = 1000$ cm$^{-1}$) is the highest with the Er:Yag laser. The $\alpha$ of other existing medical lasers ranges from 4 cm$^{-1}$ for a He-Ne laser to 600 cm$^{-1}$ for a $CO_2$ laser. Thus, the Er:Yag is widely m- 1 for a C02 viewed as the best surgical laser (see "Laser Evolution", Nov. 1991). To efficiently use the power delivered by the Er:Yag laser, a ruggedized infrared (IR) optical fiber which transmits at 2.94 microns must be used. Coupled to the output of the laser beam, the IR fiber can deliver the power to ablate tissues.

Infrared transmitting zirconium fluoride based glasses such as $ZrF_4$—$BaF_2$—$LaF_3$—$AlF_3$—$NaF$—$PbF_2$ (see Esterowitz et al, "Angioplasty With a Laser and Fiber Optics at 2-94 $\mu m$") have emerged as the materials of choice for the IR transmitting fiber because their optical transmission between 2.5 microns to 5.0 microns exceeds 90 percent, as shown in FIG. 1. Similarly, fluoride glass fibers exhibit optical losses as low as 0.06 dB/m at 2.94 microns. This is equivalent to a transmission of over 90 per cent in a one foot long fiber. A flexible fiber hand-piece with a minimum length of 6 inches and a desirable length of one foot or greater can be made adaptable to many laser delivery systems.

However, the zirconium fluoride based glass fibers have a drawback in that they are capable of carrying only very low power. Investigations recently carried out at several medical laser companies have shown the following: a 300 micron core fluoride glass fiber, when coupled to an Er:Yag laser operating with an output power of 180 mJ at a repetition rate of 10 Hz, could transmit around 135 mJ or 1.35 watts but failed after only two minutes. As the laser output power increased, the fiber damage occurred much faster. Fiber damage always occurred at the fiber input end face or along the fiber length resulting in a localized melt-down of the glass followed by power rupture. As a result, zirconium fluoride based glass fibers have a very limited use in conjunction with the Er:Yag laser, and in effect can only be used for a very short time because fiber damage quickly occurs.

It is known that $AlF_3$ used as a dopant for $ZrF_4$ base glass can increase the Tg of the glass considerably. However, the quantity of $AlF_3$ which can be incorporated as a dopant is very low, as $AlF_3$ tends to destabilize the glass and make it difficult to form into fibers. Even when formed, such fibers are not stable, as the resultant $AlF_3$ containing glass fibers tend to easily crystallize under localized heating which would inevitably occur with laser usage, thus inducing fiber damage and failure. Therefore, the addition of $AlF_3$ to the conventional $ZrF_4$ glass is not a solution to the problem of localized melt-down and resultant failure of the fiber. $AlF_3$ based glass of about 30 mol% $AlF_3$ is also known, but this glass is very unstable and difficult to form into fibers.

SUMMARY OF THE INVENTION

An object of the present invention is therefore to overcome deficiencies in the prior art, such as indicated above.

Another object of the present invention is to provide improved IR transmitting optical fibers, especially useful for laser surgery.

A further object of this invention is to provide a family of optical fibers which are transparent to IR between 1 and 3 microns and which can be used with a surgical laser, e.g. an Er:Yag laser, which operates around the main absorption band of water and which can deliver at least 1.35 watts of laser power continuously for more than ten minutes, and which optical fibers can be used to transmit laser light for precise cutting of animal, e.g. human, tissues.

A study of zirconium fluoride based optical glass fiber used with the Er:Yag laser has revealed damage induced by localized heating. When the Er:Yag laser beam was launched into the fiber, the fiber input end face was subjected to the highest power density which resulted in the overheating of surface particle defects. Such localized overheating caused the fluoride glass to soften and then partially crystallize. It was also observed that when intense overheating occurred, the tip of the fiber completely melted. The same phenomenon could apply to damage spots, especially the submicron defects in the nature of platinum particles dissolved in the glass from the melt crucible or microscopic bubbles and crystalline impurities, present along the length of the fiber.

It has thus been determined according to the present invention that in order to prevent such localized heating that would eventually damage the fiber, high temperature glasses having high glass transition temperature (Tg), thus high softening and high crystallization temperatures, and capable of transmitting at 2.94 microns, must be used as the fiber material. In addition, these glasses must have a high glass forming ability, i.e. a low tendency toward devitrification or crystallization. High grade and improved laser grade surgical fibers have therefore been developed according to the present invention based on three concepts: (1) proper choice of fiber material, i.e. high working temperature and stable glass, containing proper dopants to provide excellent IR transmission at 2.94 microns; (2) determining preferred processing techniques to enhance the 2.94 micron optical transmission; and (3) determining preferred techniques for producing the surgical fiber in large commercial quantities.

In general, the glasses of the present invention should be substantially water-free (less than 0.1 ppm of water), have a Tg of at least 290° C. and preferably at least 315° C., and a coupling efficiency[1] of at least 20% and preferably at least 35% and most preferably at least 50% over an optical path length of 1 foot; in this respect, the transmission should be at least 40% and preferably at least 50% over an optical path length of 1 foot. In addition, the glass should have a critical cooling rate, Rc, of less than 5.5° C./min and preferably less than 3.0° C./min, where Rc is defined as the slowest cooling rate at which a glass melt can be quenched without inducing crystallization. In this way the glass fiber will be able to deliver at least 1.35 watts of laser power continuously for at least five minutes and preferably more than ten minutes, efficiently and without failure.

[1] "Coupling efficiency" as here used takes into account not only attenuation losses through the fiber, i.e. percent transmission through the fiber, but also reflection losses at the fibers ends.

DETAILED DESCRIPTION OF THE INVENTION

Figure 1:
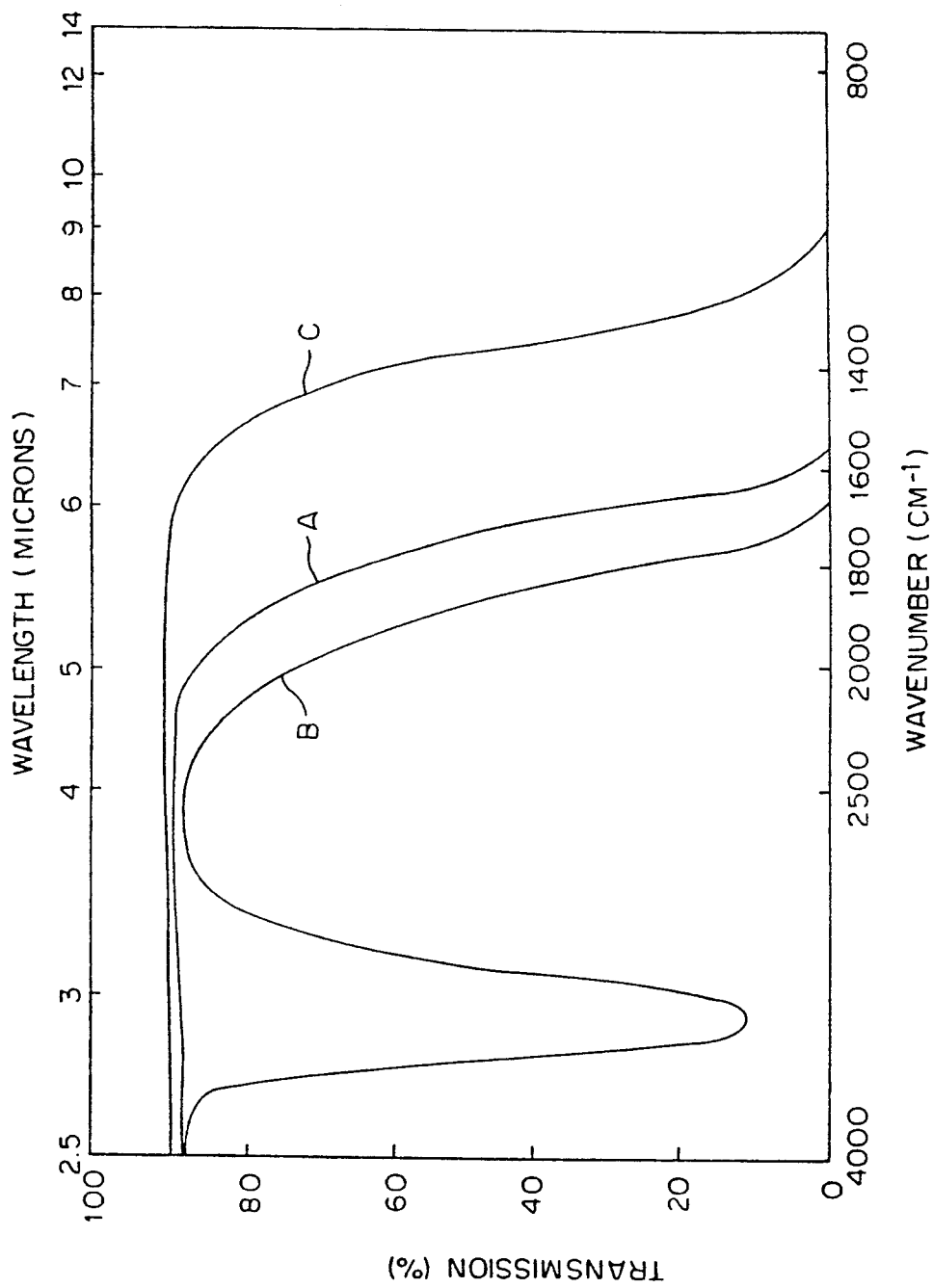
FIG. 1 is a comparative graph showing transmission percent plotted against wavelength in microns for three different glasses.

The preferred materials in the present invention are glasses based on or containing $GeO_2$, $TeO_2$, $Sb_2O_3$, PbO, $Bi_2O_3$, $Al_2O_3$, $P_2O_5$, $Al(PO_3)_3$, $M(PO_3)_2$ where M is Mg, Ca, Ba or Sr, and $NPO_3$ where N is Li, Na or K. Most preferred are those based on $GeO_2$. These oxide glasses, hereinafter referred to as heavy-metal oxide glasses, generally exhibit a glass transition temperature (Tg) and a glass stability much higher than the Tg and the glass stability in zirconium fluoride based glasses. As a result, localized heating which damages the fiber is prevented.

However, glasses formed entirely of one of these preferred oxides, especially those of lower molecular weight, do have a drawback in that their multiphonon absorption edge or infrared cut-off edge is only slightly above 2.94 microns. This will undermine transmission at 2.94 microns especially in a fiber as long as one foot. The absorption of infrared energy depends on atomic vibrations and follows Hooke's law which may be expressed as:

$$v \alpha \sqrt{\frac{f}{\mu}} \text{ with } \lambda = \frac{1}{v}$$

where
$v$ = absorbing frequency (cm-1)
$\lambda$ = absorbing wavelength (microns)
$f$ = force constant or bond strengths
$\mu$ = average mass of all ions To push the infrared absorption edge toward longer wavelengths, the forces of attraction between ions should be low, i.e. the mass of the ions should be high. To overcome this problem, the heavy-metal oxide glasses are doped with even heavier cations or anions or both to stabilize the heavy-metal oxide ions and reduce their vibrations at the atomic level when stimulated by IR. While it has been previously known that adding heavy metal ions to glass in general will push the infrared cut-off edge toward longer wavelengths, this concept has never been previously used, insofar as is known, to increase the transmission of IR at 2.94 μm in heavy-metal oxide glasses, especially in connection with laser usage.

The most preferred glass of the present invention is an oxide glass where $GeO_2$ is the glass former. The only $GeO_2$ fiber known to have been developed prior to the present invention originated from the work of H. Takahashi and I. Sugimoto, "Decreased Losses in Germanium-Oxide Glass Optical Fiber Prepared by VAD Method", *Japanese Journal of Applied Physics*, Vol. 22, No. 3 (Mar. 83) pp L139-L140. This fiber was doped with 20 mol% antimony (Sb) and was intended for telecommunication applications at 2.4 microns. At 2.94 microns, the loss of transmission of light through the fiber (i.e. the attenuation) was high, i.e. 10 dB/m, so that it transmits only about 44% of the IR through a length of one foot. It also has about 12% reflection losses at both ends, thus reducing its coupling efficiency to only 32%. Its use with an Er:Yag laser would thus result in low power transmission.

To increase the transmission at 2.94 microns, it is necessary to push the infrared cut-off edge of the $GeO_2$ glass toward longer wavelengths. To do so, it is absolutely necessary to substitute part of $GeO_2$ with dopants containing either larger and heavier cations than Ge which has an atomic weight of 72.6, or larger and heavier anions than 0 (such as F, Cl, Br, I) or a combination of both. As regards the larger and heavier cations, it will be understood that a smaller quantity of a larger and heavier cation will accomplish the same result as a larger quantity of a cation which is not so heavy. Thus, smaller quantities of Pb, Bi, Te, Hf, La, Ba, etc., having an atomic weight of about 125 and greater will accomplish the same extension of the infrared cut-off edge as will larger quantities of cations having an atomic weight above 73 but less than about 125, such Zr, Sb, As, Sr, Ca, Cd, Y, etc. Thus, for example as noted above, the use of 20 mol% of $Sb_2O_3$ as a dopant for $GeO_2$ (80 mol%), as in the case of the Takahashi et al glass, did not push the infrared cut-off edge as far as most desirable.

Dopants having either or both lighter cations and anions, such as ZnO or $TiO_2$, etc. can be added to the glass in small amounts to modify glass properties, such as stability, hardness, etc.; but the addition of lighter compounds does not contribute to the transmission of 2.94 micron IR. Typical germanate glass compositions of the present invention are shown in Table 1.

TABLE 1

| Types Of Germanate Glass | $GeO_2$ | PbO | $PbF_2$ | NaF | $AlF_3$ | $TeO_2$ | $ZrO_2$ | $La_2O_3$ | BaO | $Bi_2O_3$ | $Sb_2O_3$ | $As_2O_3$ | $SrF_2$ | $ZnO_2$ | $CaF_2$ | $PbCl_2$ |
|---|---|---|---|---|---|---|---|---|---|---|---|---|---|---|---|---|
| I | 43 | 57 | | | | | | | | | | | | | | |
| II | 61 | 24 | 15 | | | | | | | | | | | | | |
| III | 60 | | | | | | | | | | | 40 | | | | |
| IV | 40 | 56 | | | | 4 | | | | | | | | | | |
| V | 40 | 56 | | | | | | | | | | | 4 | | | |
| VI | 54 | 8 | | | | | | | 38 | | | | | | | |
| VII | 38 | 56 | | | | | 6 | | | | | | | | | |
| VIII | 43 | 49 | 8 | | | | | | | | | | | | | |

TABLE 1-continued

TYPICAL GERMANATE GLASSES OF THE INVENTION

| Types Of Germanate Glass | GeO$_2$ | PbO | PbF$_2$ | NaF | AlF$_3$ | TeO$_2$ | ZrO$_2$ | La$_2$O$_3$ | BaO | Bi$_2$O$_3$ | Sb$_2$O$_3$ | As$_2$O$_3$ | SrF$_2$ | ZnO$_2$ | CaF$_2$ | PbCl$_2$ |
|---|---|---|---|---|---|---|---|---|---|---|---|---|---|---|---|---|
| IX | 73 | | | | | | | | | | | | | | 27 | |
| X | 42 | 5 | | | | | | | | | 53 | | | | | |
| XI | 32 | 48 | | | 20 | | | | | | | | | | | |
| XII | 25 | 35 | | | | | | | | | | 40 | | | | |
| XIII | 80 | | | | | | | | | 20 | | | | | | |
| XIV | 32 | 28 | | | | 40 | | | | | | | | | | |
| XV | 20 | 30 | | | | | | | | | | | | | | 50 |
| XVI | 50 | 30 | | | | | | | | | 20 | | | | | |
| XVII | 50 | | 25 | | | | | | | | 25 | | | | | |
| XVIII | 60 | | | | | | | | | 20 | 20 | | | | | |
| XIX | 18 | 79 | | | | | 3 | | | | | | | | | |

From Table 1 it will be apparent that the amount of GeO$_2$ can vary considerably, dependent on the co-component dopants. If one or more of very heavy compounds such as PbO, PbF$_2$, PbCl$_2$, Bi$_2$O$_3$ are used as the dopants, then the quantity of GeO$_2$ may even exceed 80 mol%, whereas if the dopants are of a lighter weight the quantity of GeO$_2$ should preferably not exceed about 75%. The excellent stability provided by GeO$_2$ diminishes when the content of GeO$_2$ becomes less than about 10 mol%. The suitability of various glass compositions can be determined by routine experimentation, based on the teachings of the present disclosure.

Besides the germanate glasses, there are other heavy-metal oxide glasses that are effective with the Er:Yag laser. The other heavy-metal oxide glasses of this invention include tellurate glasses, phosphate and fluorophosphate glasses, antinonate glasses, bismuth and lead glasses and aluminate glasses. These, however, suffer from one or more difficulties as pointed out below.

The tellurates are glasses which contain TeO$_2$ as the glass network former. TeO$_2$ glass by itself does not transmit well at 2.94 microns but the addition of dopants having larger and heavier cations than Te or larger and heavier anions than O, or both, results in a much higher 2.9 micron transmission. Examples of such a glass are 60TeO$_2$-10PbO-30ZnF$_2$ and 20TeO$_2$-20PbO-20ZnF$_2$-40V$_2$O$_3$. As noted above, dopants having lighter cations, such as V$_2$O$_3$, can be incorporated into the glass to increase its stability against devitrification. The tellurate glasses have a drawback in that Te is a highly toxic chemical.

Glasses that contain P$_2$O$_5$ as the glass former are referred to as phosphate glasses. Glasses that contain Al(PO$_3$)$_3$ or M(PO$_3$)$_2$ where M=Mg, Ca, Ba, Sr, or NPO$_3$ where N=Li, Na, K, are referred to as fluorophosphate glasses. Both of these glasses exhibit a large absorption band at 4.8 microns as a result of the P-O absorption (see FIG. 5). This absorption band will adversely affect the glass transmission at 2.94 microns especially in a one foot long fiber. Therefore, to optimize the fiber transmission at 2.94 microns, the (P-O) concentration in these phosphate and fluorophosphate glasses must be kept as small as possible. Examples of phosphate and fluorophosphate with small (P-O) contents are 10P$_2$O$_5$-60CaF$_2$-30AlF$_3$ and 1.7Al(PO$_3$)$_3$-38.3AlF$_3$-10NaF-8MgF$_2$-27CaF$_2$-7SrF$_2$-8BaF2. In general, the (P-O) content should not exceed about 10 mol%.

The antinonates are glasses that contain Sb$_2$O$_3$ as the glass former. The infrared cut-off edge is at longer wavelengths for antimonate glasses than the comparable germanate glass since Sb is much heavier than Ge. Sb$_2$O$_3$ glass by itself, however, exhibits a poor glass forming ability. To stabilize the Sb$_2$O$_3$ glass, other oxide dopants such as Al$_2$O$_3$ and R$_2$O where R is Li, Na or K must be added. Examples of such glasses are 45Sb$_2$O$_3$-20Al$_2$O$_3$-35Na$_2$O and 50Sb$_2$O$_3$-18Al$_2$O$_3$-26K$_2$O-6Na$_2$O. Note also that GeO$_2$ can also be incorporated into the Sb$_2$O$_3$ glass to enhance its stability.

Antimonate glass is also receptive to dopants having anions which are heavier than O, i.e. F, Br, Cl and I. Such dopants will move the infrared edge of the glass toward longer wavelengths and therefore will enhance the glass transmission at 2.94 microns. Examples of such glasses are 80Sb$_2$O$_3$-20PbCl$_2$; 70Sb$_2$O$_3$-30PbBr$_2$; 70Sb$_2$O$_3$-30PbI$_2$; 80Sb$_2$O$_3$-20MnF$_2$; 80Sb$_2$O$_3$-20ZnF$_2$; 80Sb$_2$O$_3$-20ZnF$_2$ and 80Sb$_2$O$_3$-20SrCl$_2$.

Bismuth and lead glasses contain Bi$_2$O$_3$ and PbO as glass network formers. Bi and Pb are large and heavy elements thus contributing to the high transparency of these glasses at 2.94 microns. However, bismuth and lead glasses have the drawback that they are relatively unstable and have high refractive indices which contribute to lower coupling efficiency than other heavy-metal oxide glasses. Dopants having lighter cations such as Ga$_2$O$_3$, CdO, SiO$_2$ are added to prevent crystallization. Examples of such glasses are 61Bi$_2$O$_3$-13Ga$_2$O$_3$-26CdO; 25Bi$_2$O$_3$-57.5PbO-17.5Ga$_2$O$_3$ and 85PbO-15Al$_2$O$_3$.

Aluminate glasses contain Al$_2$O$_3$ as the primary glass former. Secondary glass formers include CaO, TiO$_2$, Nb$_2$O$_5$ and Ta$_2$O$_5$. Al is lighter than Bi, Pb, Sb, Te and Ge thus contributing to a lower transmission at 2.94 microns. The incorporation of dopants having larger and heavier cation than Al such as BaO, ZrO$_2$, PbO and Bi$_2$O$_3$ or larger and heavier anion than O such as PbF$_2$ and AlF$_3$, or both, enhances the transmission at 2.94 microns; and because Al is so relatively light, in general the aluminate glasses should not usually contain more than about 60 mol% Al$_2$O$_3$. Examples of such glasses are: 35.9Al$_2$O$_3$-59.4CaO-4.7BaO; 32.5Al$_2$O$_3$-55.2CaO-7.0BaO-5.3PbO; 27Al$_2$O$_3$-64CaO-7Bi$_2$O$_3$-2AlF$_3$; 20Al$_2$O$_3$-40Ta$_2$O$_5$-40K$_2$O; 15Al$_2$O$_3$-42.5Nb$_2$O$_5$-42.5K$_2$O; and 25.02Al$_2$O$_3$-19.83TiO$_2$-19.83Ta$_2$O$_5$-4.12ZrO$_2$-12.46BaO-9.37K$_2$O-9.37Na$_2$O.

The heavy-metal oxide glasses have another conventional drawback in that they invariably contain small amounts of water which are originally bonded to the raw oxide starting materials and/or which become incorporated into the glass during melting in the atmosphere. Since water absorbs strongest at 2.94 microns, trace amounts of it can undermine the ability of the glass to transmit at 2.94 microns, especially in a one foot or longer fiber, as this problem becomes increasingly severe as the path length through the glass increases.

To eliminate the presence of water and water absorption, the heavy-metal oxide glasses must be processed in a water-free atmosphere, e.g. a dry glove box atmosphere of argon or nitrogen. The weighing and batching of the chemicals, and the melting of the glass must be conducted in a dry atmosphere of less than 0.1 ppm water. Prior to the present invention, heavy-metal oxide glasses were generally processed in air, thus picking up moisture from the atmosphere.

It is known to use fluoride dopants such as $PbF_2$ or $AlF_3$ in heavy metal oxide glass to minimize the water content. Thus, in addition to dry melting according to the present invention, one or more halide compounds such as a fluoride and/or a chloride may be added to enhance the water removal. However, the use of a halide alone is not adequate. Another technique to enhance water removal and for the drying of the raw materials according to the present invention is to use a reactive gas such as fluorine or chlorine, at low temperatures of less than 100° C. to prevent conversion of oxide to fluoride or chloride.

Two techniques can be used successfully to fiberize the heavy-metal oxide glasses. The rotational casting process described by Tran et al in U.S. Pat. No. 5,055,120 (1991) is very efficient in making glass preforms from heavy-metal oxide glasses the viscosities of which are less than 50 poises at the melt temperature. In this process, the cladding glass melt is poured into a metallic mold which is subsequently rotated to form a tube. The core melt is then poured into the tube to form a preform. Finally the preform is drawn into fibers using an electric furnace.

The second approach, called the double crucible method, as described in "Material Systems, Fabrication and Characteristics of Glass Fiber Optical Waveguide" by Merle D. Rigterink, *Ceramic Bulletin*, Vol. 55, No. 9 (1976), is preferred when the cladding glass melt cannot be rotated to form a perfect tube, i.e. when the melt viscosity is relatively high at the melt temperature. The double crucible technique consists of loading the core glass in the inner crucible and the cladding glass in the outer crucible. Both crucibles are equipped with a small nozzle at the bottom and are concentric to each other. The crucible set-up is heated to the glass softening temperature in an electric furnace. Core and cladding glasses can then be drawn down from the crucible nozzles.

The following examples, offered illustratively only, further explain the present invention. In the following examples all transmission curves were obtained from glass samples which were ground and polished to a thickness of 2 mm.

EXAMPLE 1

Used as starting chemicals were $GeO_2$, PbO and $PbF_2$. Twenty-five grams in total of these materials were used to prepare a germanate glass the final composition of which was $56GeO_2$-29PbO-15PbF_2$. The chemical powder wall weighed and mixed in a platinum crucible inside a glove box filled with argon. The water content of the glove box was less than 0.1 ppm. The crucible was capped with a platinum lid then placed inside an electric furnace located within the glove box and was heated to 1100° C. and soaked for three hours. The resulting molten glass was cast into a cylindrical mold, 1.5 cm in diameter, which was maintained at an annealing temperature of 330° C. The mold was then cooled slowly to room temperature. The glass disc thus obtained was used for characterization.

By way of comparison, (1) a 25 g germanate glass containing $80GeO_2$-20Sb_2O_3$ according to Takahashi et al was prepared using the same procedure described above; and (2) a 25 g zirconium fluoride based glass containing $53ZrF_4$-18BaF_2$-3LaF_3$-3AlF_3$-18NaF-5PbF_2$ was melted under the same conditions as above except that the temperature at which the components were melted was 875° C. and the temperature of the mold into which the mold was cast was 263° C.

Using a Perkin-Elmer DSCII differential scanning calorimeter, the glass transition temperatures (Tg) and the critical cooling rates of the three glasses were determined. As expected, the Tgl's of the germanate glasses, 600° C. for the $GeO_2$-Sb_2O_3$ glass and 330° C. for the $GeO_2$-PbO-PbF_2$ glass, were higher than that of the fluoride glass which was only 263° C. The Rc's of the two germanate glasses were about 2.5° C./min whereas the Rc of the fluoride glass was about 5° C./min.

The optical transmission curves plotted in FIG. 1 show the infrared edge of each of the three glass samples. The infrared cut-off edge is defined as the wavelength at which the transmission starts to decrease. The infrared cut-off edge of the Takahashi et al $GeO_2$-Sb_2O_3$ sample is 4.1 microns (Curve B), and the closest to 2.94 microns. When heavy compounds of PbO and $PbF_2$ were substituted, the edge shifted toward 4.7 microns (Curve A) thus enhancing significantly the transmission at 2.94 microns in a long fiber. The fluoride glass (Curve C) is most transparent with an infrared cut-off edge of 5.8 microns, but such fluoride glass has too low a Tg.

It should be noted that dry melting alone did not eliminate water in the glass. This is shown by the large water absorption band located at 2.9 microns in the case of $GeO_2$-Sb_2O_3$ glass sample (Curve B). The addition of fluoride such $PbF_2$, as in the case of the $GeO_2$-PbO-PbF_2$ glass sample, combined with dry melting, resulted in elimination of the water. In the later case, F reacted with OH from the water to form HF.

EXAMPLE 2

Used as starting materials were $GeO_2$ and $Sb_2O_3$. Twenty-five grams in total of these oxides were used to prepare a heavy-metal oxide glass containing the Takahashi et al composition of $80GeO_2$-20Sb_2O_3$. Inside a glove box with an argon atmosphere of less than 0.1 ppm water, the chemical powder was weighed, mixed and then placed in a Teflon beaker. A reactive gas, fluorine in this case although other water-reactive gases can be used, was passed slowly through the powder via a small Teflon tube, about 5mm inside diameter. The beaker was heated to around 70° C. After eight hours, the powder was transferred to a capped platinum crucible and melted using the same procedure of Example 1.

Figure 2:
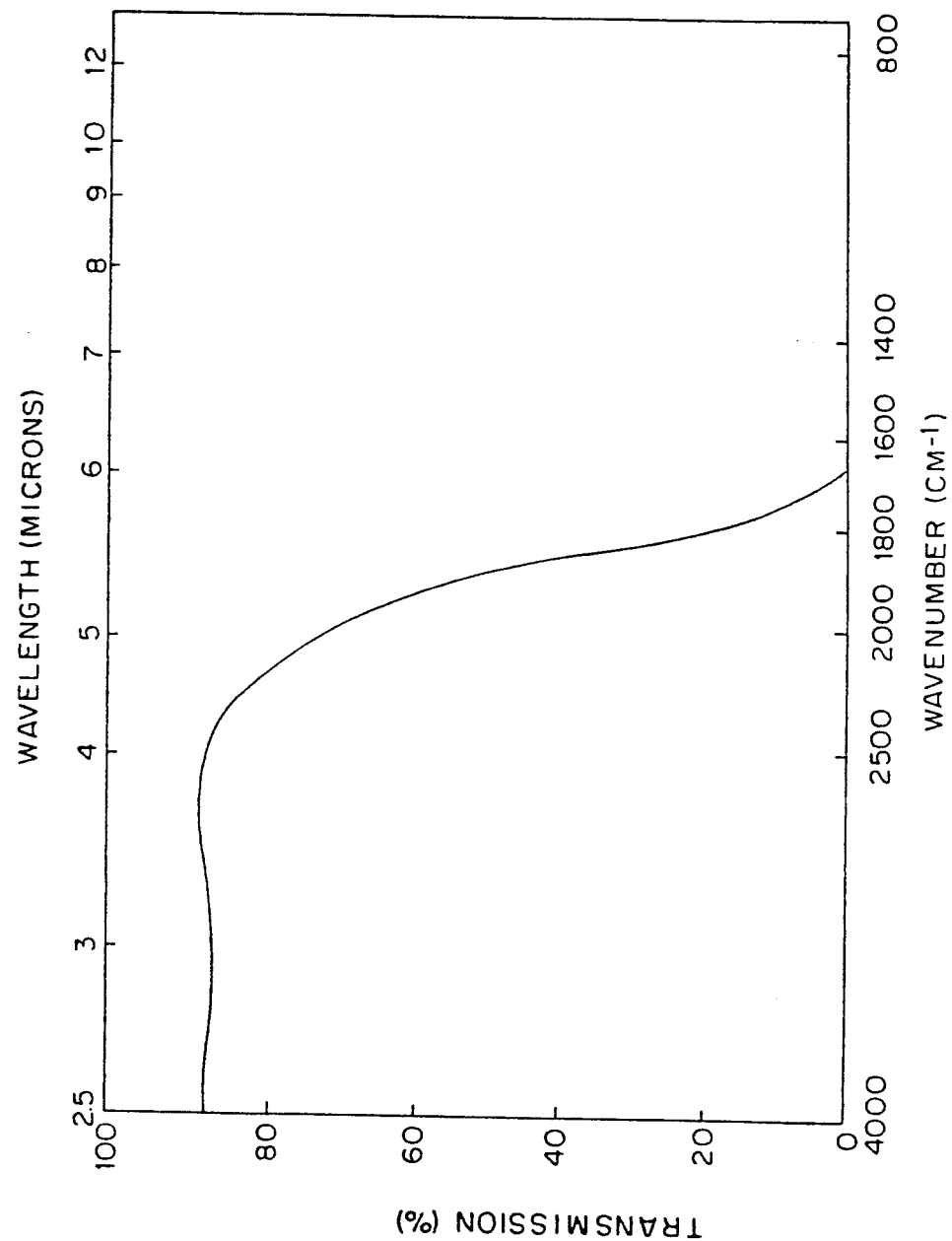
FIG. 2 is a similar graph showing the results with pretreatment with fluorine.

The transmission curve for the glass sample is plotted in FIG. 2. When compared with the transmission curve for the same compositional glass but without fluorine treatment (Curve B shown in FIG. 1), it is clear that fluorine treatment combined with dry melting enhances the water removal from the glass.

EXAMPLE 3

Figure 3:
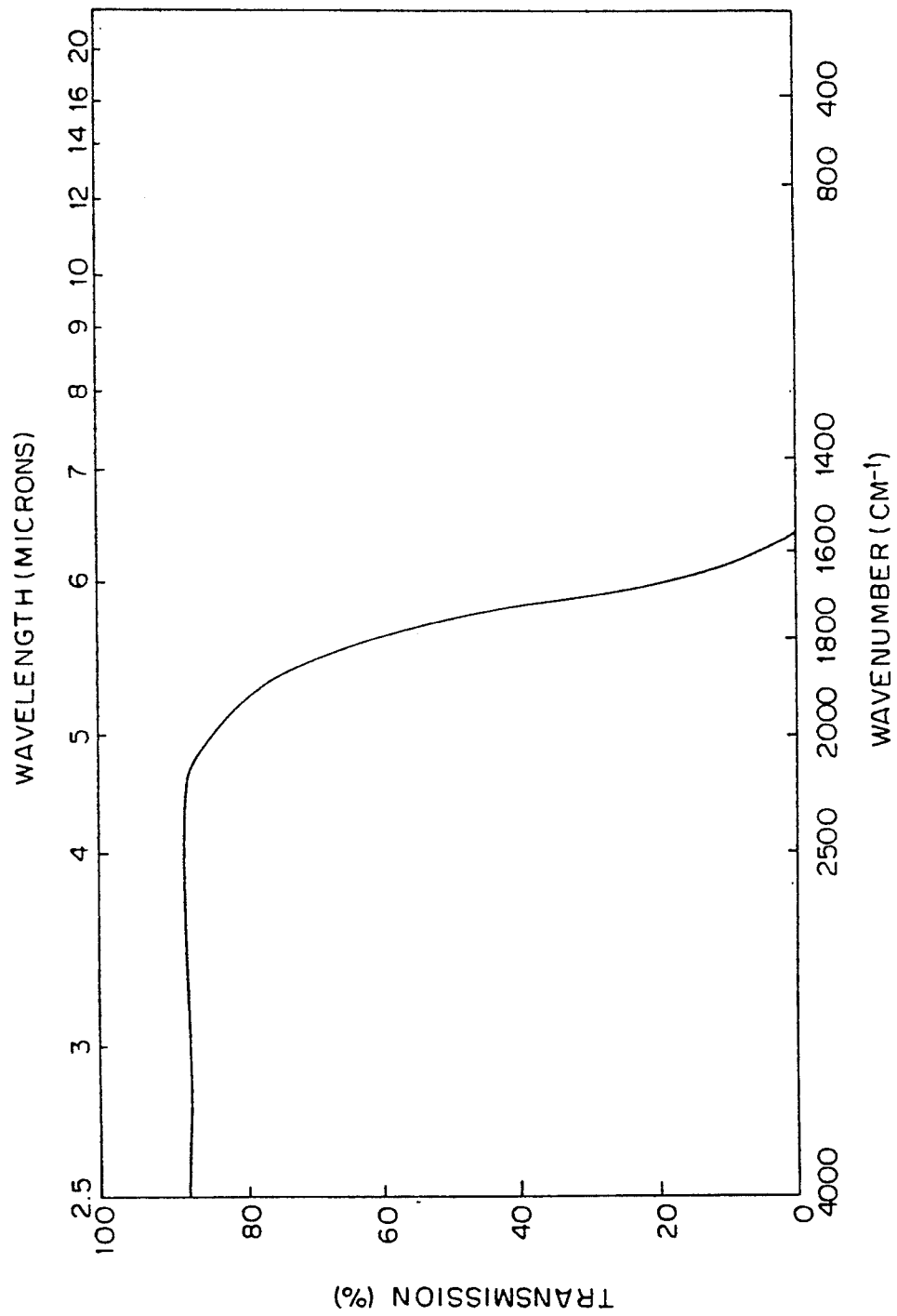
FIG. 3-10 are similar graphs for other glasses.

A 25 g germanate glass containing $30GeO_2$-50PbO-18AlF_3$-2PbF_2$ was melted under the same conditions as in Example 1. Its transmission characteristics shown in FIG. 3 and its Rc value are very similar to those of the 56GeO$_2$-29PbO-15PbF$_2$ glass of Example 1, except that its Tg of 380° C. is higher.

EXAMPLE 4

Figure 4:
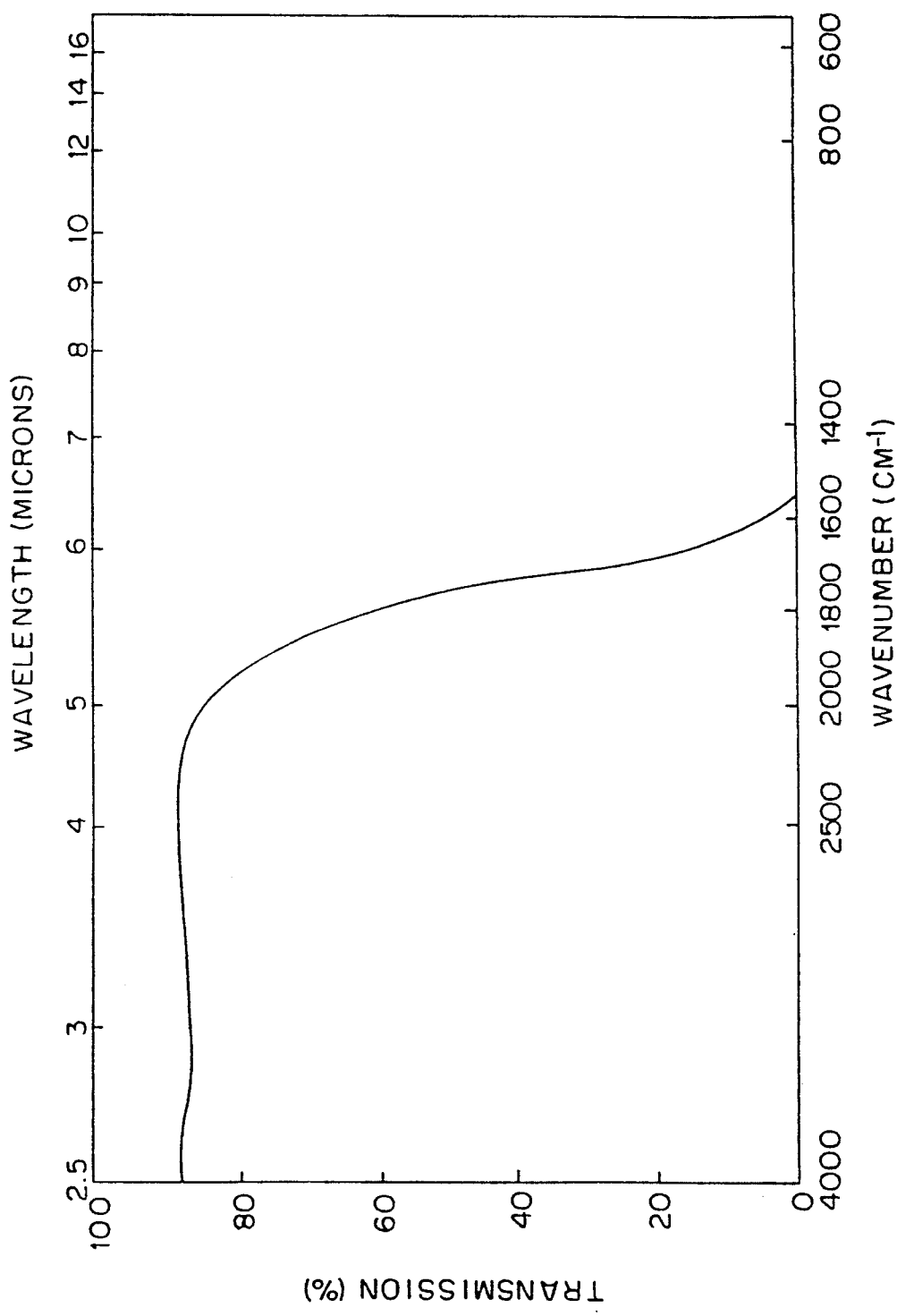

Used as starting materials were Sb$_2$O$_3$, PbO, PbF$_2$ and GeO$_2$. Twenty-five grams in total of these chemicals were used to prepare a germanate glass containing 25Sb$_2$O$_3$-25PbF$_2$-50GeO$_2$. The batching and melting procedures were similar to the ones used in Example 1. The transmission curve obtained for the glass is plotted in FIG. 4. The Tg and Rc of the glass obtained by differential scanning calorimetry was 310° C. and 2.5° C./min, respectively.

EXAMPLE 5

Figure 5:
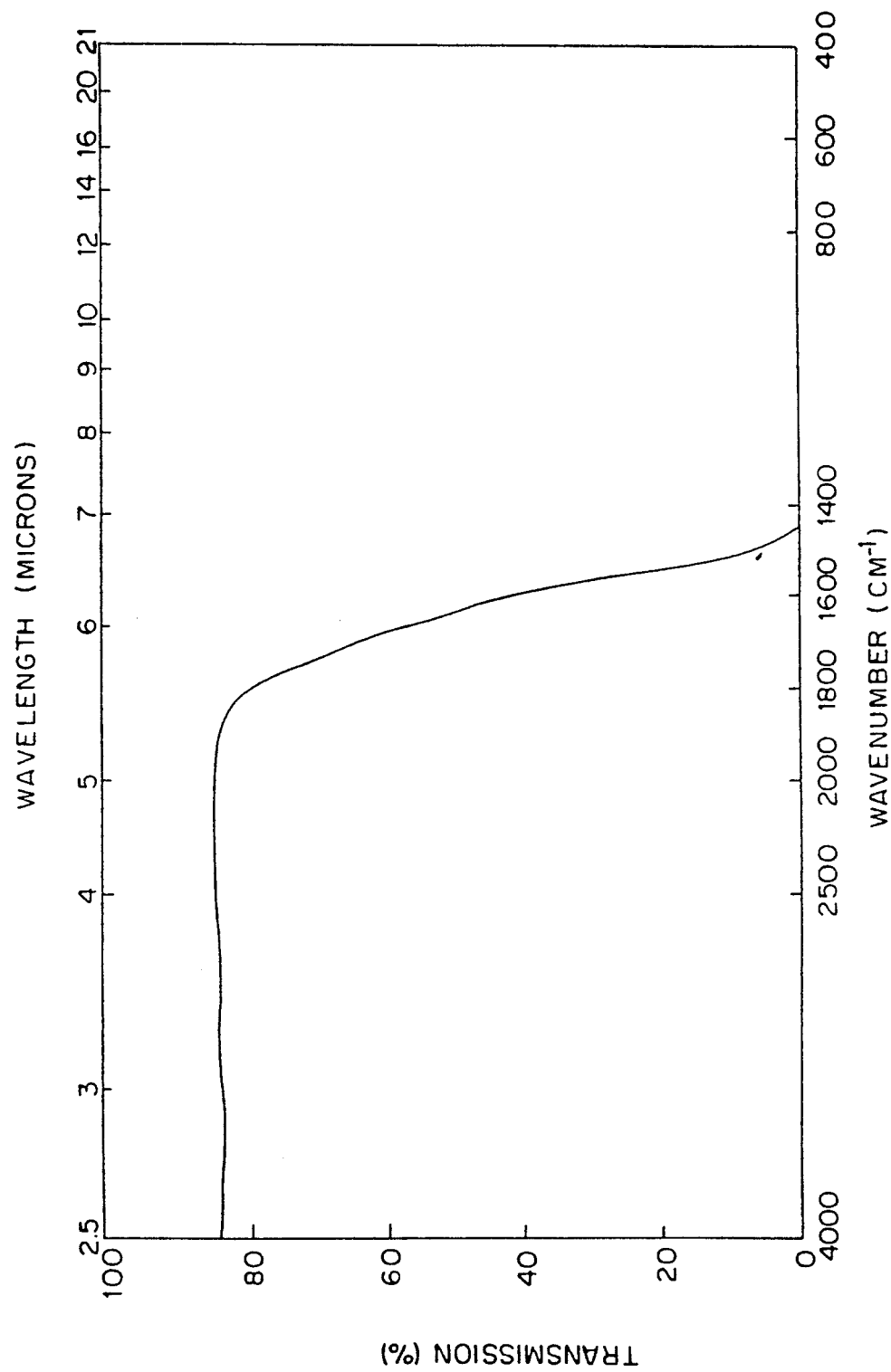

A 25 g tellurate glass containing 57TeO$_2$-13PbO-28ZnF$_2$-2PbF$_2$ was melted under the same conditions as in Example 1. The transmission curve obtained from the glass sample plotted in FIG. 5 shows an extended infrared cut-off edge as compared to that of the glasses of Examples 1 and 3, which was attributed to the heavier Te cation. Using differential scanning calorimetry, a Tg value of 350° C. and an Rc value of 3° C./min were obtained.

EXAMPLE 6

Figure 6:
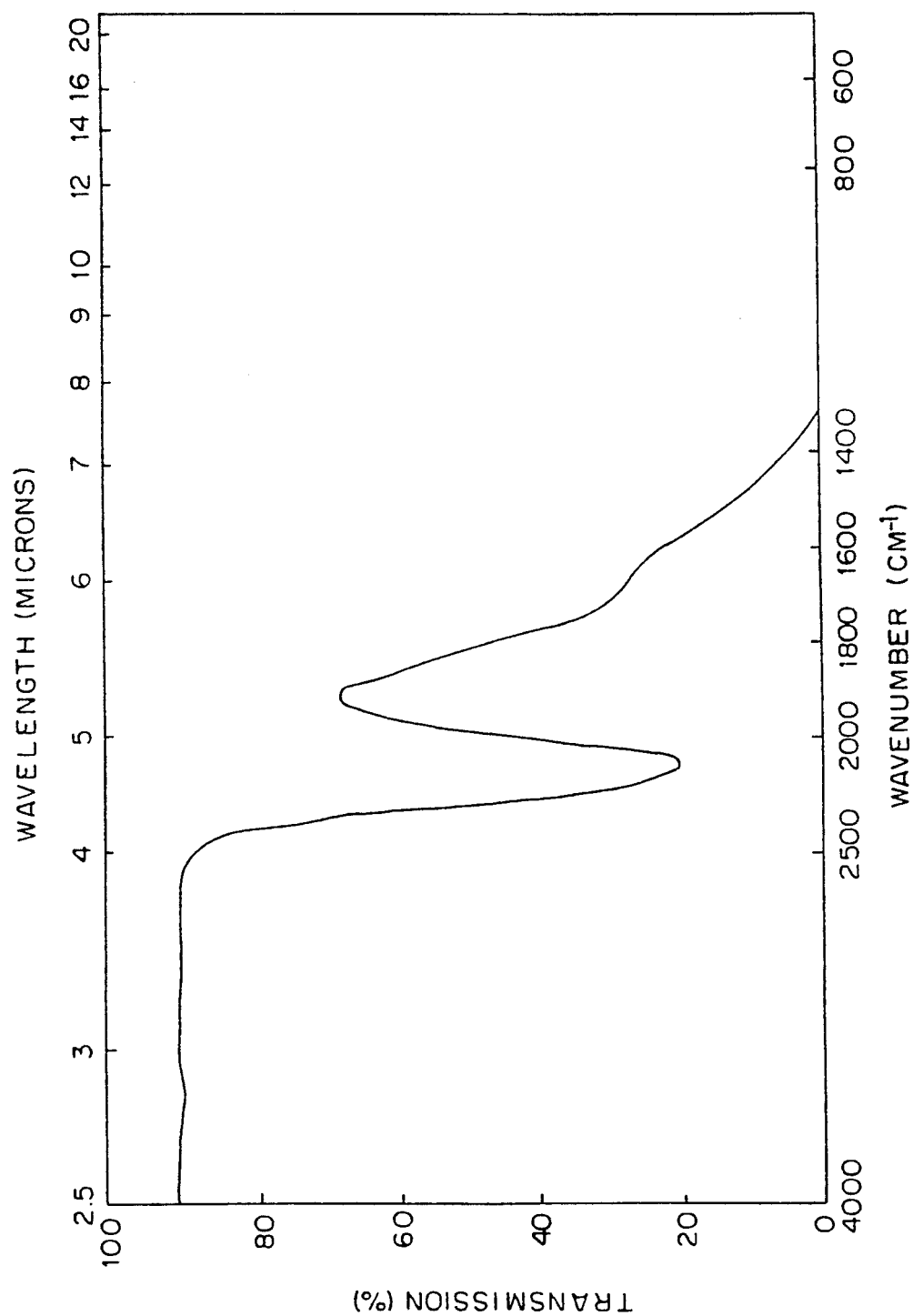

Used as starting materials were P$_2$O$_5$, CaF$_2$, and AlF$_3$. Twenty-five grams in total of these materials were used to prepare a phosphate glass containing 60CaF$_2$-26.5AlF$_3$-3.5PbF$_2$-10P$_2$O$_5$. The batching and melting procedures were similar to the ones used in Example 1. The transmission curve for the glass plotted in FIG. 6 shows an absorption band at 4.8 microns due to P-O and an infrared cut-off edge at about 4 microns, making this glass barely suitable, i.e. suitable only for short length fibers of 6 inches or shorter. The Tg and Rc of the glass obtained by differential scanning calorimetry were 448° C. and 3° C./min respectively.

EXAMPLE 7

Figure 7:
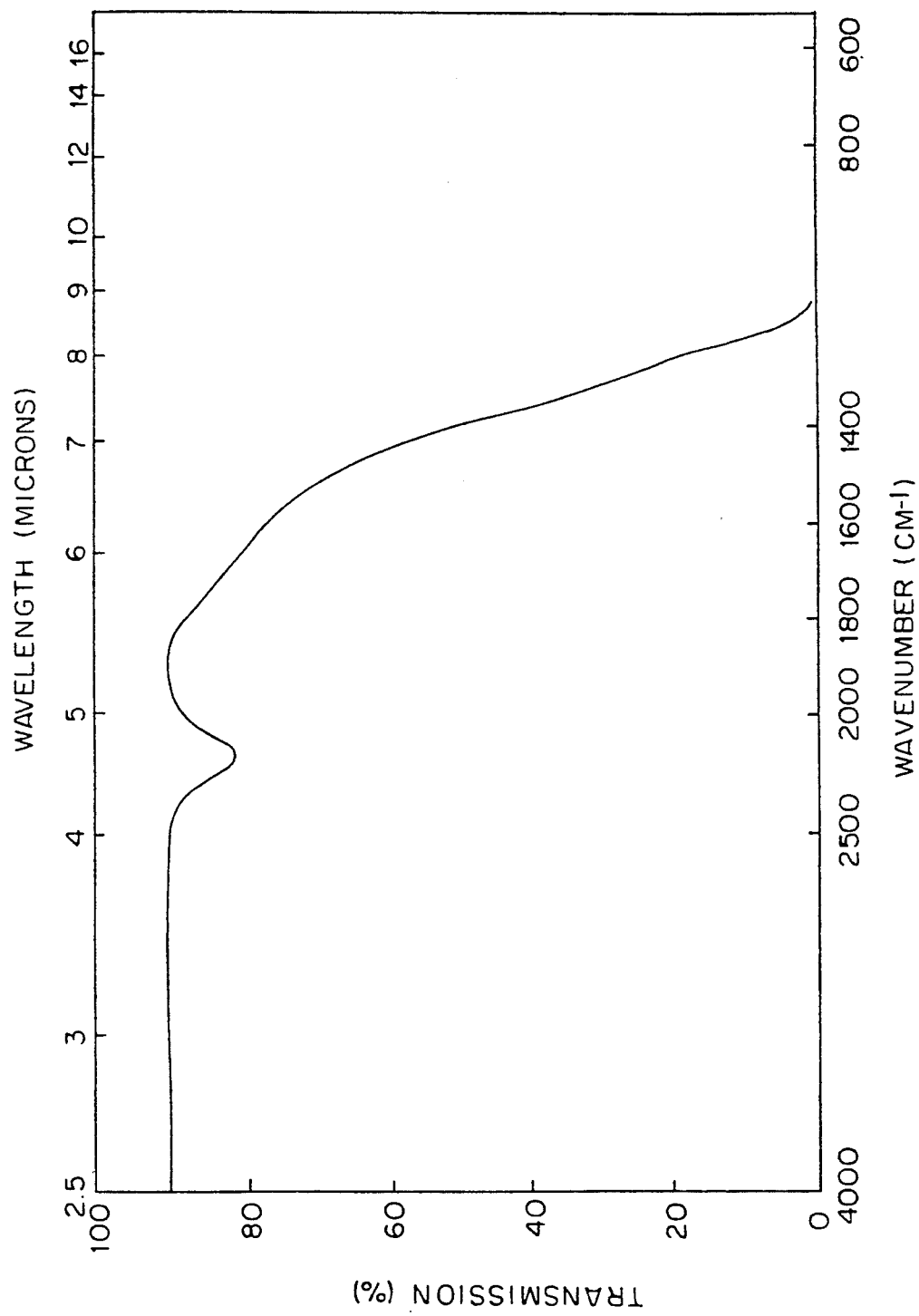

Used as starting materials were Al(PO$_3$)$_3$, AlF$_3$, ZrF$_4$, BaF$_2$, CaF$_2$, SrF$_2$, YF$_3$, MgF$_2$, NaF and PbF$_2$. Twenty-five grams in total of these chemicals were used to prepare a fluorophosphate glass containing 0.2Al(PO$_3$)$_3$-29AlF$_3$-10.2ZrF$_4$-9.8BaF$_2$-18.3CaF$_2$-12SrF$_2$-8.3YF$_3$-3.5MgF$_2$-3.8NaF-5PbF$_2$. The batching and melting procedures were similar to the ones used in Example 1. The transmission curve for the glass plotted in FIG. 7 shows an absorption band at 4.8 microns due to P-O. This absorption band is smaller than the one obtained for the phosphate glass of Example 5 because of a smaller (P-O) concentration. The Tg and Rc of the glass obtained by differential scanning calorimetry were 390° C. and 4.5° C./min, respectively. The presence of so much AlF$_3$, needed in this glass to increase the Tg to an acceptable level, tends to severely de-stabilize the glass, and the phosphate is needed to permit stable fiber manufacture.

EXAMPLE 8

Figure 8:
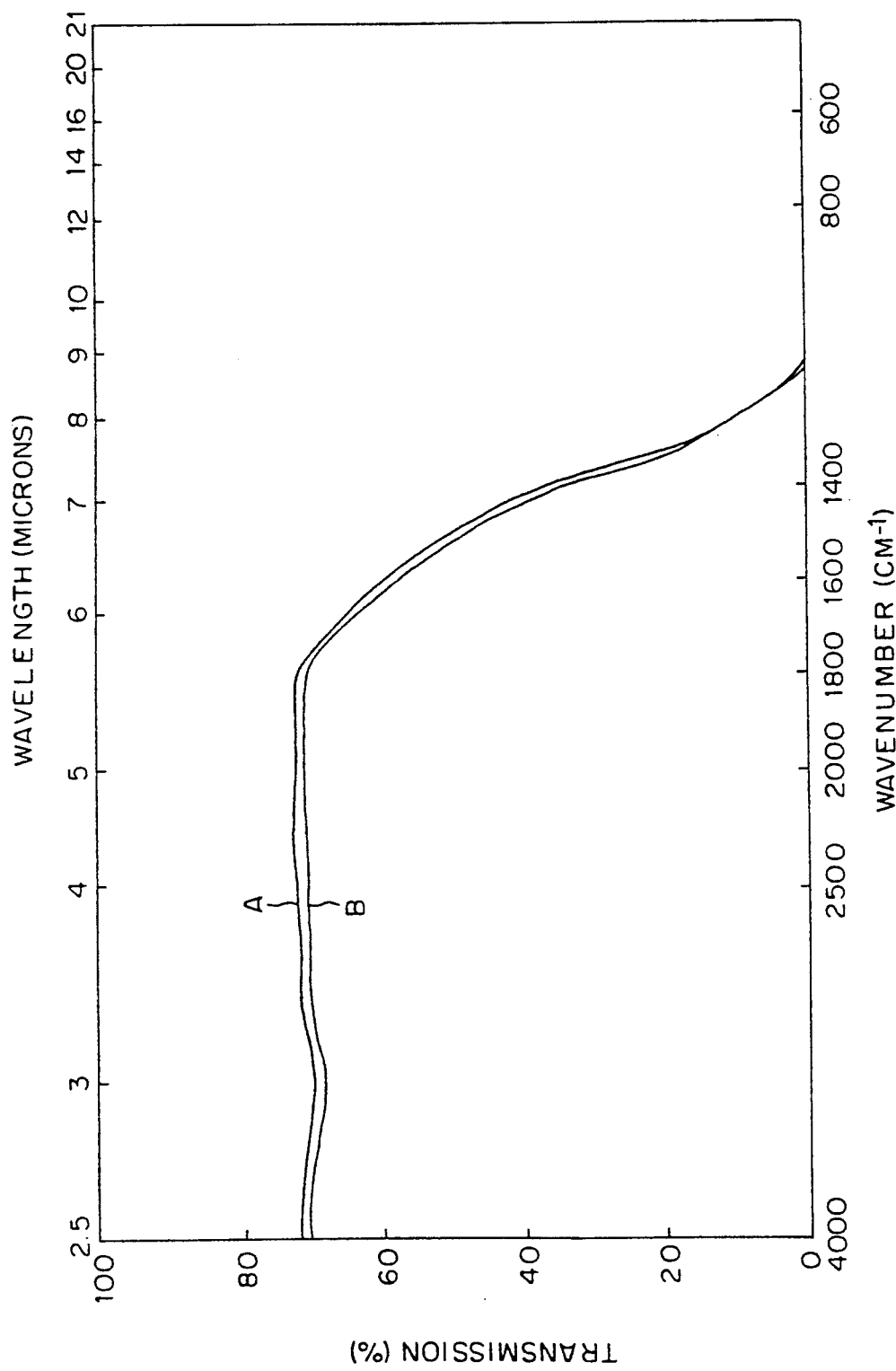

Used as starting oxides were Bi$_2$O$_3$, PbO, CdO and Ga$_2$O$_3$. Twenty-five grams in total of the oxides were used to prepare a bismuth glass containing 61Bi$_2$O$_3$-26CdO-13Ga$_2$O$_3$, and 25 g in total of the oxides were used to prepare a lead-bismuth glass containing 25Bi$_2$O$_3$-57.5PbO-17.5Ga$_2$O$_3$. The batching and melting procedures are similar to the ones described in Example 2. The transmission curves for both glass samples are plotted in FIG. 8. The Tg's of the bismuth and lead-bismuth glasses, obtained by differential scanning calorimetry, were 375° C. and 350° C., respectively. The Rc's of both glasses were about 3.5° C./min.

EXAMPLE 9

Figure 9:
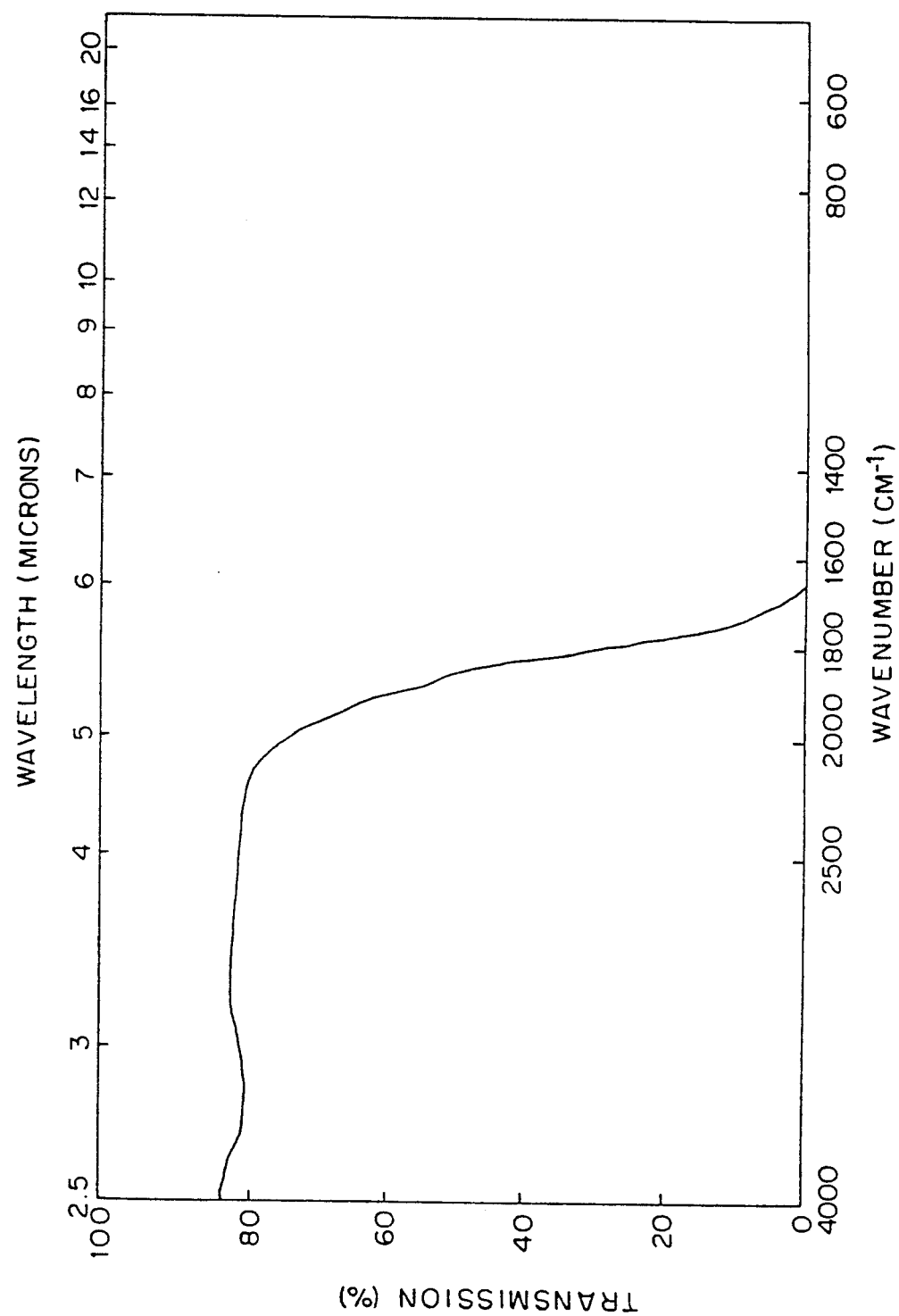

Used as starting oxides were Al$_2$O$_3$, Ta$_2$O$_5$ and K$_2$O. Twenty-five grams in total of these materials were used to prepare an aluminate glass containing 20Al$_2$O$_3$-40Ta$_2$O$_5$-40K$_2$O. The batching and melting procedures were similar to the ones used in Example 2, except that the melt temperature was raised to 1500° C. The transmission curve obtained for the glass sample is plotted in FIG. 9. The Tg and Rc of the glass, obtained by differential scanning calorimetry, were 525° C. and about 5° C./min, respectively.

EXAMPLE 10

Figure 10:
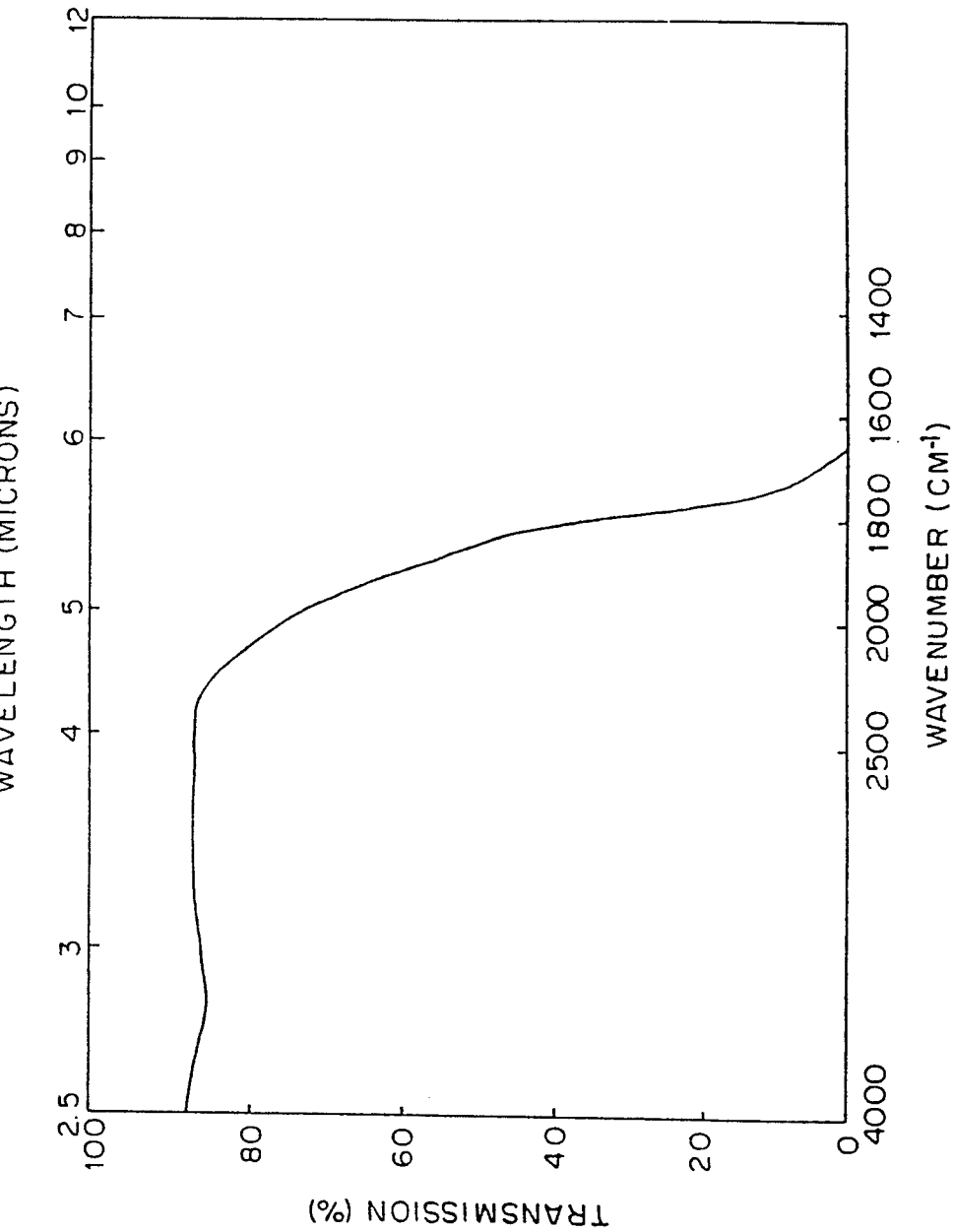

Used as starting oxides were Sb$_2$O$_3$, Al$_2$O$_3$, KNO$_3$ and Na$_2$CO$_3$. Twenty-five grams in total of these materials were used to prepare an antimonate glass containing 50Sb$_2$O$_3$-18Al$_2$O$_3$-26K$_2$O-3Na$_2$O-3Li$_2$O. The batching and melting procedures were similar to the ones used in Example 2. The transmission curve for the glass is plotted in FIG. 10. The Tg and Rc value obtained by differential scanning calorimetry was 403° C. and 4° C./min, respectively.

EXAMPLE 11

The germanate glass of Example 1, 56GeO$_2$-29PbO-15PbF$_2$ (Fiber No. 1); the germanate glass of Example 2 (Fiber No. 2) 80GeO$_2$-20Sb$_2$O$_3$; the germanate glass of Example 3 (Fiber No. 3), 30GeO$_2$-50PbO-18AlF$_3$-2PbF$_2$; the germanate glass of Example 4 (Fiber No. 4), 25Sb$_2$O$_3$-25PbF$_2$-50GeO$_2$; the tellurate glass of Example 5 (Fiber No. 5), 57TeO$_2$-13PbO-28ZnF$_2$-2PbF$_2$; the phosphate glass of Example 6 (Fiber No. 6), 60CaF$_2$-26.5AlF$_3$-3.5PbF$_2$-10P$_2$O$_5$; the fluorophosphate glass of Example 7 (Fiber No. 7), 0.2Al(PO$_3$)$_3$-29AlF$_3$-10.2ZrF$_4$-9.8BaF$_2$-18.3CaF$_2$-12SrF$_2$-8.3YF$_3$-3.5MgF$_2$-3.8NaF-5PbF$_2$; the bismuth glass of Example 8 (Fiber No. 9), 61Bi$_2$O$_3$-26CdO-13Ga$_2$O$_3$; the lead-bismuth glass of Example 8 (Fiber No. 9), 25Bi$_2$O$_3$-51.5PbO-17.5Ga$_2$O$_3$; the aluminate glass of Example 9 (Fiber No. 10), 20Al$_2$O$_3$-40Ta$_2$O$_5$-40K$_2$O; and the antinonate glass of Example 10 (Fiber No. 11) 50Sb$_2$O$_3$-18Al$_2$O$_3$-26K$_2$O-3Na$_2$O-3Li$_2$O were used as the core material for the making of optical fiber for laser surgery. By way of comparison, the fluoride glass of Example 1 (Fiber No. 12), 53ZrF$_4$-18BaF$_2$-3LaF$_3$-3AlF$_3$-18NaF-5PbF$_2$, was also used as a core material for the making of a fluoride glass optical fiber.

The cladding material for each fiber was the same type of glass as the core glass except the concentration of one or two components in each respective glass was altered to lower the glass refractive index. The core and cladding glass compositions of each type of fiber and its respective numerical aperture (NA) are given in Table 2. Twenty-five grams of each of the cladding glass were made using the same batching and melting procedures used for the core glass.

TABLE 2

Core and cladding glass compositions used in the fabrication of heavy-metal oride glass fibers.

| Fiber No. | Glass Type | (Core)/(Clad) Composition (mol %) | NA |
|---|---|---|---|
| 1 | Germanate | (56GeO$_2$—29PbO—15PbF$_2$)/(61GeO$_2$—24PbO—15PbF$_2$) | 0.20 |
| 2 | Germanate | (80GeO$_2$—20SB$_2$O$_3$)/(100GeO$_2$) | 0.48 |
| 3 | Germanate | (32GeO$_2$—50PbO—18AlF$_3$—2PbF$_2$)/(32GeO$_2$—48PbO—20AlF$_3$) | 0.19 |
| 4 | Germanate | (25Sb$_2$O$_3$—25PbF$_2$—50GeO$_2$)/(25Sb$_2$O$_3$—21.5PbF$_2$—53.5GeO$_2$) | 0.20 |
| 5 | Tellurate | (57TeO$_2$—13PbO—28ZnF$_4$—2PbF$_2$)/(60TeO$_2$—10PbO—30ZnF$_2$) | 0.20 |
| 6 | Phosphate | (60CaF$_2$—26.5AlF$_3$—3.5PbF$_2$—10P$_2$O$_5$)/(60CaF$_2$—30AlF$_3$—10P$_2$O$_5$) | 0.19 |
| 7 | Fluorophosphate | [0.2Al(PO$_3$)$_3$—29AlF$_3$—10.2ZrF$_4$—9.8BaF$_2$—18.3CaF$_2$—12SrF$_2$—8.3YF$_3$—3.5MgF$_2$—3.8NaF—5PbF$_2$]/[0.2Al(PO$_3$)$_3$—10ZrF$_4$—10BaF$_2$—18CaF$_2$—13SrF$_2$—8YF$_3$—3.3MgF$_2$—3.5NaF] | 0.20 |
| 8 | Bismuth | (61Bi$_2$O$_3$—26CdO—13Ga$_2$O$_3$)/(55Bi$_2$O$_3$—28CdO—13Ga$_2$O$_3$—4PbO) | 0.19 |
| 9 | Lead-Bismuth | (25Bi$_2$O$_3$—57.5PbO—17.5Ga$_2$O$_3$)/(28Bi$_2$O$_3$—56PbO—16Ga$_2$O$_3$) | 0.21 |
| 10 | Aluminate | (20Al$_2$O$_3$—40Ta$_2$O$_5$—40K$_2$O)/(30Al$_2$O$_3$—35Ta$_2$O—17.5K$_2$O—17.5Na$_2$O) | 0.12 |
| 11 | Antimonate | (50Sb$_2$O$_3$—18Al$_2$O$_3$—26K$_2$O—3Na$_2$O—3Li$_2$O/(48Sb$_2$O$_3$—18Al$_2$O$_3$—26K$_2$O—6Na$_2$O) | 0.18 |
| 12 | Fluoride | (53ZrF$_4$—18BaF$_2$—3CaF$_3$—3AlF$_3$—18NaF—5PbF$_2$)/(53ZrF$_4$—20BaF$_2$—4LaF$_3$—3AlF$_3$—20NaF) | 0.20 |

EXAMPLE 12

The rotational casting technique was used to prepare Fibers 1, 3 through 7 and 12 of the Table 2 because of their low melt viscosities. In each case, 23 g of cladding glass and 25 g core glass were used to make a preform 6.5 cm long and 1 cm in diameter. The pre-melts for cladding and core glasses were remelted for two hours at a temperature $T_{melt}$. The cladding melt wall cast into a mold pre-heated a temperature $T_{mold}$ which was about the glass transition temperature. The mold was then spun and the melt solidified to form a cladding tube. The rotational casting process parameters $T_{melt}$, are given in Table 3 for each of the Fibers from 1, 3 through 7 and 12.

TABLE 3

Preform processing and draw parameters used in the fabrication of the heavy-metal oxide glass fibers.

| Fiber No. | Preform Type | $T_{melt}$ (°C.) | $T_{mold}$ (°C.) | $T_{draw}$ (°C.) |
|---|---|---|---|---|
| 1 | Germanate | 950 | 330 | 420 |
| 3 | Germanate | 950 | 380 | 450 |
| 4 | Germanate | 950 | 310 | 400 |
| 5 | Tellurate | 1050 | 350 | 510 |
| 6 | Phosphate | 1000 | 445 | 625 |
| 7 | Fluorophosphate | 1000 | 390 | 535 |
| 12 | Fluoride | 800 | 263 | 330 |

The core melt was subsequently poured into the tube to form a preform having a waveguide structure. The preform was then drawn into fiber at a temperature $T_{draw}$ in an electric furnace flushed with a dry argon atmosphere. The fiber was coated with UV-acrylate buffer to preserve its mechanical strength. All fibers obtained had a core diameter of 325 microns and a clad diameter of 525 microns, ±8 microns.

The double crucible technique was applied in the fabrication of Fibers 2 and 8 through 11 because of their high melt viscosities. The double crucible set up consisted of a small platinum crucible concentrically placed inside a larger crucible. The inside diameters of the inner and outer crucibles were 2 cm and 4 cm, respectively. The bottoms of the inner and outer crucibles were tapered to form a nozzle measuring 1.9 mm and 2.2 mm, respectively. The double crucible set-up was placed inside an electric furnace flushed with dry argon gas and was pre-heated at a temperature $T_{draw}$ which was the softening or working temperature of the glass.

The pre-melts for cladding and core glasses were remelted for two hours at a temperature $T_{melt}$. The cladding melt and core melt were cast into the outer crucible and inner crucible, respectively. The melts rapidly cooled down to the working point and were drawn down into fibers having a 325 micron core and a 525 micron clad, ±15 microns. The fiber was coated in-line with a UV acrylate buffer to preserve its mechanical strength.

The double crucible draw parameters are given in Table 4 for each of the Fibers 2 and 8 through 11.

TABLE 4

Double crucible draw parameters used in the fabrication of the heavy-metal oxide glass fibers.

| Fiber No. | Glass Type | $T_{melt}$ (°C.) | $T_{draw}$ (°C.) |
|---|---|---|---|
| 2 | Germanate | 1150 | 825 |
| 8 | Bismuth | 1000 | 475 |
| 9 | Lead-Bismuth | 1000 | 435 |
| 10 | Aluminate | 1100 | 750 |
| 11 | Antimonate | 1100 | 615 |

EXAMPLE 13

The fibers prepared using the methods of Example 11 were characterized in terms of their optical transmission. Using a Nerst glower, a monochromater, infrared filters and an InSb detector, the fiber loss measurements were carried out at 2.06 microns and 2.94 microns, using the conventional fiber cut-back technique. In the cut-back technique, the light transmission through a long fiber, $T_{long}$, was first measured. The fiber was then cut into a shorter length, and the light transmission through the short fiber, $T_{short}$, was recorded. The fiber attenuation, $\alpha$, expressed in dB/m was obtained as follows:

$$(dB/m) = \frac{1}{L_2 - L_1} 10 \ln \frac{T_{short}}{T_{long}}$$

when
$L_2$ = length of the long fiber
$L_1$ = length of the short fiber

The measured attenuation for each of the fibers of Example 11 is set forth in Table 5.

TABLE 5

Measured attenuation for each of the surgical fibers.

| Fiber No. | Glass Type | $\alpha$(dB/m) at 2 microns | $\alpha$(dB/m) at 2.94 microns |
|---|---|---|---|
| 1 | Germanate | 1.1 | 2.9 |
| 2 | Germanate | 0.8 | 10 |
| 3 | Germanate | 0.9 | 2.7 |

TABLE 5-continued

| Measured attenuation for each of the surgical fibers. | | | |
|---|---|---|---|
| Fiber No. | Glass Type | α(dB/m) at 2 microns | α(dB/m) at 2.94 microns |
| 4 | Germanate | 1.0 | 2.9 |
| 5 | Tellurate | 1.5 | 2.2 |
| 6 | Phosphate | 2.3 | 7.6 |
| 7 | Fluorophosphate | 0.2 | 0.5 |
| 8 | Bismuth | 3.2 | 5.1 |
| 9 | Lead-Bismuth | 4.6 | 6.9 |
| 10 | Aluminate | 4.8 | 8.3 |
| 11 | Antimonate | 1.9 | 3.7 |
| 12 | Fluoride | 0.1 | 0.06 |

As can be seen from Table 5 above, the attenuation α for Germanate Fiber No. 2 at 2.94 microns was 10 dB/m. According to an article by Drexhage and Moynihan entitled "Infrared Optical Fibers" appearing in *SCIENTIFIC AMERICAN*, November 1988, at page 116, one part per million (1 ppm) of hydroxyl ion causes an attenuation of 10 dB/m at 2.9 microns. Therefore, in view of Fiber No. 2, the amount of water in the fibers of the present invention must be less than 1 ppm.

EXAMPLE 14

The 325 micron core and 525 micron clad optical fibers prepared using the methods of Example 11 were tested for their power handling capability using an Er:Yag laser and an Ho:Yag laser. The Er:Yag and Ho:Yag lasers emit 250 micro-second pulses of radiation at 2.94 microns and at 2.06 microns, respectively, and deliver a maximum of 500 NJ per pulse in multimode operation. Each fiber under test was carefully cleaned until two good ends were obtained. The laser radiation $I_i$ was coupled to the fiber via a $CaF_2$ lens combination having a 22 mm focal length. The output energy, $I_o$, was measured with a radiometer set to measure ten consecutive pulses. A repetition rate of 10 Hz was used. The duration of the laser operation was stretched to a maximum of twenty minutes to avoid damaging the laser cavity. The resulting values of $I_i$, $I_o$, the fiber length under test, the power coupling efficiency and the condition of each fiber after the test are given in Table 6 for the Er:Yag laser and in Table 7 for the Ho:Yag laser.

TABLE 6

| Power handling characteristics of heavy-metal oxide glass fibers as compared to fluoride glass fiber using an Er:Yag laser. | | | | | |
|---|---|---|---|---|---|
| Fiber No. | Glass Type | $I_i$ (mJ) | $I_o$ (mJ) (1 ft length) | coupling efficiency (1 ft length) | Fiber Conditions |
| 1 | Germanate | 500 | 340 | 68% | No damage observed after maximum duration of test of twenty minutes. |
| 2 | Germanate | 500 | 160 | 32% | No damage observed after maximum duration of fifteen minutes. |
| 3 | Germanate | 500 | 360 | 72% | No damage observed after maximum duration of test of twenty minutes. |
| 4 | Germanate | 500 | 350 | 70% | No damage observed after maximum duration of test of twenty minutes. |
| 5 | Tellurate | 500 | 345 | 68% | No damage observed after maximum duration of test of twenty minutes. |
| 6 | Phosphate | 500 | 260 | 52% | No damage observed after maximum duration of test of twenty minutes. |
| 7 | Fluorophosphate | 500 | 440 | 88% | No damage observed after maximum duration of test of twenty minutes. |
| 8 | Bismuth | 500 | 175 | 35% | No damage observed after maximum duration of test of twenty minutes. |
| 9 | Lead-Bismuth | 500 | 135 | 27% | No damage observed after maximum duration of test of twenty minutes. |
| 10 | Aluminate | 500 | 200 | 40% | No damage observed after maximum duration of test of twenty minutes. |
| 11 | Antimonate | 500 | 300 | 60% | No damage observed after maximum duration of test of twenty minutes. |
| 12 | Fluoride | 500 | 450 | 90% | Input ends melted, fiber fractured after 1 min 05 sec. |

TABLE 7

| Fiber No. | Glass Type | $I_i$ (mJ) | $I_o$ (mJ) (1 ft length) | coupling efficiency (1 ft length) | Fiber Conditions |
|---|---|---|---|---|---|
| 1 | Germanate | 500 | 390 | 78% | No damage observed after maximum duration of test of twenty minutes. |
| 2 | Germanate | 500 | 412 | 82% | No damage observed after maximum duration of fifteen minutes |
| 3 | Germanate | 500 | 410 | 82% | No damage observed after maximum duration of test of twenty minutes. |
| 4 | Germanate | 500 | 410 | 82% | No damage observed after maximum duration of test of twenty minutes. |
| 5 | Tellurate | 500 | 365 | 73% | No damage observed after maximum duration of test of twenty minutes. |
| 6 | Phosphate | 500 | 385 | 77% | No damage observed after |

TABLE 7-continued

| Fiber No. | Glass Type | $I_i$ (mJ) | $I_o$ (mJ) (1 ft length) | coupling efficiency (1 ft length) | Fiber Conditions |
|---|---|---|---|---|---|
| 7 | Fluorophosphate | 500 | 447 | 89.5% | maximum duration of test of twenty minutes. No damage observed after maximum duration of test of twenty minutes. |
| 8 | Bismuth | 500 | 225 | 45% | No damage observed after maximum duration of test of twenty minutes. |
| 9 | Lead-Bismuth | 500 | 180 | 36% | No damage observed after maximum duration of test of twenty minutes. |
| 10 | Aluminate | 500 | 280 | 56% | No damage observed after maximum duration of test of twenty minutes. |
| 11 | Antimonate | 500 | 350 | 70% | No damage observed after maximum duration of test of twenty minutes. |
| 12 | Fluoride | 500 | 450 | 90% | Both input and output ends developed craters after 1 min. 33 sec. power quickly dropped to zero. |

The results from these tests indicate that all heavy metal oxide glass fibers of this invention exhibit power handling much longer than the fluoride glass fiber which is absolutely required in laser surgery, although their power transmission efficiency is lower due to their higher attenuation at 2.94 microns and 2.06 microns. The fluoride glass fiber on the other hand could deliver 90% of the laser output power but was considered useless because of its almost instantaneous degradation. The fluoride glass fiber breaks down after only 1-1.5 minutes when coupled to an Er:Yag laser at an output power of about 3 watts, required for many surgical procedures. The power handling ability of the present heavy metal oxide glass fibers is a first time result in this field, insofar as known.

The test results of Table 6 also show that the power transmission of Fibers 2, 8 and 9 was among the lowest because fiber 2 had a high attenuation of 10 dB/m at 2.94 microns. Fibers 8 and 9 on the other hand had lower attenuation but very high refractive indices of 2.43 and 2.46, respectively. These high refractive indices contributed a total of about 35% reflection loss at the two ends of fibers 8 and 9. To increase the coupling efficiencies, the ends of fibers 8 and 9 can be coated with a standard anti-reflection coating that will reduce the total reflection loss of the two fibers to about 10%.

All the heavy-metal oxide glasses of the present invention exhibited transmission in the 90% range between 1 to 3 microns over a 2mm optical path length and at least 27% over 1 foot optical path length. The optical attenuation of the heavy-metal oxide glass fibers increases as the operational wavelength decreases toward 1 micron, since the infrared absorption cut-off edge becomes weaker at shorter wavelengths. This behavior is apparent from the test results of Tables 6 and 7 which show that the fiber coupling efficiency was higher at 2.06 microns than at 2.94 micron. As a result the heavy-metal oxide glass fibers can be efficiently used in conjunction with any surgical lasers covering the 1 to 3 microns operational wavelength region.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. In a surgical laser operating in the mid-infrared wavelength region of between 1.0 and 3.0 microns and including an optical fiber for transmitting laser light, the improvement wherein said optical fiber has a solid core and a cladding, and is formed of a glass containing less than 1 ppm of $H_2O$ and having a glass transition temperature Tg of at least 290° C., comprising a heavy metal oxide and having a coupling efficiency of at least 20% over an optical path length of one foot, said glass having a critical cooling rate Rc of less than 5.5° C./min, said optical fiber constituting means for delivering at least 1.35 watts of laser power continuously for at least five minutes and without failure.

2. A surgical laser according to claim 1, wherein said optical fiber has a length of at least six inches.

3. A surgical laser according to claim 1, wherein said optical fiber has a length of at least one foot.

4. A surgical laser according to claim 1, said glass comprising 10-85 mol% $GeO_2$ and at least one dopant selected from the group consisting of PbO, $PbF_2$, NaF, $AlF_3$, $TeO_2$, $ZrO_2$, $La_2O_3$, BaO, $Bi_2O_3$, $Sb_2O_3$, $As_2O_3$, $SrF_2$, $ZnO_2$, $CaF_2$ and $PbCl_2$.

5. A surgical laser according to claim 1, wherein said optical fiber is capable of transmitting IR at 1.0 to 3.0 microns of at least 40% over a one foot optical length.

6. A surgical laser according to claim 1, wherein said glass has a Tg of at least 315° C. and said optical fiber has a coupling efficiency of at least 35% over a one foot length.

7. A surgical laser according to claim 6, wherein said Rc is less than 3.0° C./min and said coupling efficiency is at least 50% over a one foot length.

8. A surgical laser according to claim 1, wherein said glass contains less than 0.1 ppm of $H_2O$.

9. A surgical laser according to claim 1, wherein said glass further comprises an amount sufficient of a fluoride dopant to minimize the water content of said glass.

* * * * *